United States Patent
Ogawa et al.

(10) Patent No.: US 7,680,524 B2
(45) Date of Patent: Mar. 16, 2010

(54) MAGNETIC FLUID DETECTION METHOD AND MAGNETIC FLUID DETECTION APPARATUS

(75) Inventors: Junichi Ogawa, Akita (JP); Yoshihiro Minamiya, Akita (JP); Yoshihisa Katayose, Akita (JP); Reijiro Saito, Akita (JP); Shuichi Kamada, Akita (JP); Tomoaki Ueda, Kyoto (JP)

(73) Assignee: Olympus Corporation, Tokyo (JP)

(*) Notice: Subject to any disclaimer, the term of this patent is extended or adjusted under 35 U.S.C. 154(b) by 2084 days.

(21) Appl. No.: 10/277,022

(22) Filed: Oct. 21, 2002

(65) Prior Publication Data

US 2003/0078493 A1 Apr. 24, 2003

(30) Foreign Application Priority Data

Oct. 23, 2001 (JP) ............................. 2001-324788

(51) Int. Cl.
*A61B 5/05* (2006.01)
*G01R 33/02* (2006.01)

(52) U.S. Cl. .................... 600/409; 600/420; 324/259

(58) Field of Classification Search ............... 600/419, 600/420, 409; 330/252; 702/189; 324/256, 324/259, 301

See application file for complete search history.

(56) References Cited

U.S. PATENT DOCUMENTS

| | | | |
|---|---|---|---|
| 3,932,805 A * | 1/1976 | Abe et al. .................. | 324/309 |
| 4,185,237 A * | 1/1980 | Uehara et al. ............... | 324/317 |
| 4,827,945 A   | 5/1989 | Groman et al. | |
| 5,732,704 A * | 3/1998 | Thurston et al. ............ | 600/431 |
| 5,794,622 A * | 8/1998 | Chopp et al. ................ | 600/431 |

FOREIGN PATENT DOCUMENTS

| | | |
|---|---|---|
| JP | 06-142964 | 5/1994 |
| JP | 8-98819 | 4/1996 |
| JP | 09-164123 | 6/1997 |

OTHER PUBLICATIONS

Patent Abstracts of Japan for Japanese Publication No. 08098819, published Apr. 16, 1996.

* cited by examiner

*Primary Examiner*—Eric F Winakur
*Assistant Examiner*—Katherine L Fernandez
(74) *Attorney, Agent, or Firm*—Scully, Scott, Murphy & Presser, P.C.

(57) ABSTRACT

The apparatus of the present invention comprises: an excitation device which excites the measurement site with a local direct-current or alternating-current magnetic field, and a plurality of magnetic field detection devices which are disposed in proximity to each other to measure the magnetic field component that is perpendicular to the exciting magnetic field. A magnetic fluid that possesses paramagnetism is injected from the outside into a substance in which a fluid can flow, and the local magnetic field gradient is then measured while the injected magnetic fluid is excited by the application of a direct-current or alternating-current magnetic field from the outside, thus measuring the presence or absence of distortion of the local magnetic field distribution arising from the fact that the specific magnetic permeability of the magnetic fluid injected into the substance is higher than that of the surrounding substance, so that sites where large amount of the magnetic fluid has accumulated are identified in a non-invasive manner without being affected by external magnetic noise.

16 Claims, 4 Drawing Sheets

MAGNETIC FLUID DETECTION METHOD AND MAGNETIC FLUID DETECTION APPARATUS

This application claims benefit of Japanese Patent Application No. 2001-324788 filed in Japan on Oct. 23, 2001, the contents of which are incorporated by this reference.

BACKGROUND OF THE INVENTION

1. Field of the Invention

The present invention relates to a magnetic fluid detection method and magnetic fluid detection apparatus which are used to measure how a magnetic fluid possessing paramagnetism, that has been injected into an area adjacent to a malignant tumor, is distributed after a fixed period of time has elapsed, to obtain evidence for identifying sentinel lymph nodes, which are lymph nodes that are positioned on the downstream side of the malignant tumor site with respect to the direction of flow of the lymph, and that are located closest to the affected area along the lymphatic vessels that constitute the flow path of the lymph.

To describe this in more detail, the present invention relates to a magnetic fluid detection method and magnetic fluid detection apparatus which can measure the distortion of the local magnetic field distribution resulting from the fact that the specific magnetic permeability of a magnetic fluid possessing paramagnetism that has been injected into tissues is higher than that of the surrounding substance, and which can in non-invasive manner identify sites where large quantities of the magnetic fluid remain without being affected by external magnetic noise, by using a magnetic fluid possessing paramagnetism such as Feridex, which is a type of iron oxide colloid known as ultra-paramagnetic fine particles used as a magnetic marker, or using a paramagnetic fluid such as MnZn ferrite, Fe3O4 magnetite or the like, then injecting this magnetic fluid possessing paramagnetism from the outside into living-body tissues through which liquids can flow, then applying a direct-current or alternating-current magnetic field to the tissues constituting the object of measurement so that the magnetic fluid is excited, and finally measuring the local magnetic field gradient.

2. Description of the Related Art

Conventionally, in surgical operations performed on breast cancers, lung cancers, esophagal cancers and the like, not only has the malignant tumor area been excised, but all of the lymph nodes surrounding the site of the malignant tumor have been excised, i.e., purified, from the standpoint of preventing recurrence of the cancer due to metastasis. The reason for such purification of surrounding lymph nodes is that cancer cells exfoliated from the affected area are carried downstream with the flow of lymph flowing through the lymphatic vessels, leading to metastasis of the cancer.

However, in the case of excision of surrounding lymph nodes, there is a danger that this will cause immune suppression in the convalescent patient, so that it is desirable to forgo such excision if possible. Accordingly, procedure known as sentinel lymph node biopsy has been devised. Sentinel lymph nodes refer to the lymph nodes that are closest to the malignant tumor site along the lymph flow path among the lymph nodes positioned on the downstream side of the malignant tumor site with respect to the direction of flow of the lymph. The sentinel lymph node biopsy refers to a biopsy in which these sentinel lymph nodes are excised and examined in order to determine whether or not cancer cells are present in these lymph nodes. If cancer cells have not reached the sentinel lymph nodes, then the malignant tumor has not progressed to the stage where cancer metastasis occurs. Accordingly, cancer cells have naturally not migrated to any of the other lymph nodes located even further downstream in the direction of flow of the lymph, so that there is no need to purify the lymph nodes. Specifically, in this case, lymph nodes other than the sentinel lymph nodes are preserved.

However, it is not always the case that the lymph nodes that are closest to the malignant tumor site in terms of distance are said sentinel lymph nodes. The lymph nodes that are closest in terms of distance are lymph nodes that are positioned on the upstream side with respect to the direction of flow of the lymph and the lymph nodes are not necessarily said sentinel lymph nodes. This depends largely on how the lymphatic vessels, which form the flow passages of the lymph, are connected. Furthermore, the lymph is colorless and transparent, and the lymphatic vessels are also extremely fine, so that identification of the sentinel lymph nodes from the direction of flow of the lymph and positional relationship of the lymph nodes is virtually impossible by visual inspection during the limited time available in the surgical operation.

Recently, in the United States, methods using radioactive isotopes and dyes have been devised in order to identify the positions of sentinel lymph nodes, and such methods have already been practical use as biopsy methods in breast cancer. In such methods, a radioactive isotope or dye is used as a marker in the area proximal to the malignant tumor; a fluid containing this isotope or dye is injected, and sentinel lymph nodes are identified by investigating the position of the radioactive isotope or areas colored by the dye after a fixed period of time has elapsed. It is necessary that the particle size of the marker be approximately 10 nm or less, which is a size that can easily be pushed downstream by the flow of the lymph through the lymphatic vessels. The position of a radioactive isotope can easily be investigated using a miniature Geiger counter, and the amount of accumulation can also be roughly judged by the intensity of the radiation. Accordingly, such methods have made it possible to identify sentinel lymph nodes by means of a simple examination using the fact that said marker shows the greatest accumulation in sentinel lymph nodes as evidence.

In Japan, however, the handling of radioactive isotopes in hospitals is restricted by law, and the number of hospitals that have received permission to use such isotopes is extremely small. Accordingly, there are difficulties in the popularization of sentinel lymph node biopsy methods that use radioactive isotopes as markers. In the case of dyes, furthermore, there may be cases in which discrimination is difficult, depending on the condition of the living-body tissue. For example, since lymph nodes in the lungs are black due to the settling of carbon particles, visual discrimination is extremely difficult in the case of dyes.

Furthermore, a SQUID magnetic flux meter using a superconducting quantum interference device (hereafter abbreviated to "SQUID") which can detect magnetic flux equal to approximately 1 in 1,000,000,000 parts of the earth's magnetism with high sensitivity has been applied in various fields, and in recent years, a high-temperature superconducting SQUID which can be utilized for cooling at the temperature of liquid nitrogen has been practical use. A method for identifying sentinel lymph nodes by using a magnetic fluid containing fine magnetic particles with residual magnetization characteristics as a magnetic marker, temporarily magnetizing this magnetic fluid by means of a strong magnetic field from the outside, and identifying sentinel lymph glands by utilizing the fact that the magnetic field arising from the residual magnetization is maintained for a short time, has been proposed by Mr. Saburo Tanaka et al. of Toyohashi Technical and Scientific University on Jan. 25, 2000. Details are reported in "Applications of High-Temperature Superconducting SQUID Microscopes in the Fields of Biotechnology and Medicine", 66th Research Conference Materials of the 146th Committee for Superconducting Electronics of the Japanese Society for the Promotion of Technology. According to the home page of the Chubu Science and Technology Center (Ltd.), this is currently being studied (as of Oct. 8, 2001) as a part of subsidy work performed by the Japanese Society for the Promotion of Bicycles. However, this method involves many problems as described below.

As the particle diameter of the magnetic particles becomes smaller, the magnitude of the residual magnetization also decreases. In the case of a particle size (diameter) of 10 nm or less, which allows easy flow through the lymphatic vessels, the residual magnetization characteristics are almost completely lost in the case of almost all known magnetic materials, so that a magnetic sensor with ultra-high sensitivity must be used in order to measure the extremely weak residual magnetism. Since an extremely weak magnetic field is measured and the measurement is also susceptible to the effects of magnetic environmental noise, measurements must be performed in a high-performance magnetically shielded room. Not only are such magnetically shielded rooms expensive, but the magnetic noise radiated by other necessary medical equipment causes interference, so that such a method is inconvenient.

Furthermore, even if the ultra-high-sensitivity magnetic sensor that is used is a high-temperature superconducting SQUID, the cooling must be performed at the temperature of liquid nitrogen, so that the sensor unit is increased in size, and also has a considerable weight, whether the cooling system used is a liquid cooling system or a refrigerator using the heat cycle of a cooling medium. Accordingly, such a system cannot be carried and operated with one hand.

Furthermore, the magnetization of the magnetic fluid must be performed so that the direction of the residual magnetization is oriented along the direction of flow of the lymphatic vessels. If this is not done, the direction of the magnetic moment quickly becomes disordered as a result of the properties of the liquid and molecular motion, so that the magnetic moment as a whole drops, thus making measurement impossible. In order to maintain the direction of magnetization of the magnetic fluid for a long period of time, excitation must be performed with a solenoid coil wrapped around the lymphatic vessels. However, the actual lymphatic vessels themselves are difficult to distinguish by visual inspection, and even assuming that visual discrimination is possible, this method involves work such as the excision of tissue and attachment required in order to wrap the coil. Moreover, considering the difficulty of insulation measures that are required in order to prevent the exciting current, which is a large current, from flowing through the human body, this method is not suitable for practical use.

Meanwhile, an ultra-paramagnetic fluid possessing the paramagnetism of an iron oxide colloid, known by the commercial name of Ferumoxides and by the formulation name of Feridex, shows a shadow-generating effect in nuclear magnetic resonance computer section imaging or MRI. The tendency of this substance to accumulate in the liver is utilized in liver contrast medium used for the local diagnosis of liver cancers, and this agent has been approved by the decision of the First Survey Council for New Drugs and the Special Council for Drugs. Besides Feridex, other known fine magnetic particles include MnZn ferrite, Fe3O4 magnetite and the like; however, only Feridex has been tested with respect to side effects on the human body, and received approval.

Theoretically, it would appear to be possible to identify the positions of sentinel lymph nodes in three dimensions by injecting these existing magnetic fluids into areas proximal to malignant tumors, and then obtaining images by MRI after a fixed period of time has elapsed. In many cases, however, the chest must be opened in order to inject the magnetic fluid into the area proximal to a malignant tumor, and because of the flow velocity of the lymph, MRI imaging must be performed within a few minutes following injection. Since the MRI apparatus itself generates an intense magnetic field, this apparatus must be kept far away from equipment and instruments that possess magnetism, and therefore cannot be installed in the operating theater. Moreover, since the lymph nodes are scattered over a broad area, the imaging range of the sectional images must also be set over a broad range, so that the imaging time is increased. In addition, such imaging cannot be completed within a few minutes following injection. For these and other reasons, this method is not utilized to identify the positions of sentinel lymph nodes.

In order to popularize sentinel lymph node biopsies, it is necessary to make it possible to identify the positions of such lymph nodes in a short time by a non-invasive measurement method using a magnetic fluid as a marker, without using radioactive isotopes. However, in the case of methods that measure the residual magnetism of a magnetic fluid, there are many theoretical and practical restrictions. The reasons for these restrictions are as follows: as the particle size decreases, the residual magnetism characteristics are also diminished, so that the magnetic signal strength that is measured drops, and the problem of magnetic environmental noise is increased. In addition, there is some physical inconvenience involved in the method used to attach the excitation coil to the living-body tissue. Moreover, because the magnetic fluid is a liquid, the orientation of the magnetic moment quickly becomes disordered following magnetization as a result of the molecular motion of the fine magnetic particles, so that the magnetic field strength attenuates.

SUMMARY OF THE INVENTION

It is an object of the present invention to provide a magnetic fluid detection method and magnetic fluid detection apparatus which can measure the distortion of the local magnetic field distribution, that results from the fact that the specific magnetic permeability of a magnetic fluid possessing paramagnetism that is injected into living-body tissues is higher than that of surrounding substance, by applying a direct-current or alternating-current magnetic field from the outside to such tissues into which a magnetic fluid has been injected, so that the magnetic fluid is excited, and then by measuring the local magnetic field gradient of the magnetic filed component that is perpendicular to the exciting magnetic field, and which can thus identify in a non-invasive manner portions of the living-body tissue in which a large amount of the magnetic fluid has accumulated, without being affected by external magnetic noise.

Furthermore, it is an object of the present invention to provide a magnetic fluid detection method and magnetic fluid detection apparatus which use a magnetic fluid as a marker, and which can detect the presence of the magnetic fluid on the basis of the variation in the gradient of the alternating-current magnetic field component that results from the fact that the specific magnetic permeability of the magnetic fluid is higher than that of surround substances so that the distribution of the magnetic field applied for the purpose of excitation is distorted, thus making it possible to identify the positions of sentinel lymph nodes simply and in a short time without using a radioactive isotope.

Furthermore, it is an object of the present invention to provide a magnetic fluid detection method and magnetic fluid detection apparatus which can reliably judge whether or not the lymph nodes in question are sentinel lymph nodes, without any inconvenience, even when the lymph nodes are black so that discrimination is difficult in the case of a dye.

Furthermore, it is an object of the present invention to provide a magnetic fluid detection method and magnetic fluid detection apparatus which can detect a magnetic fluid with high sensitivity while canceling out magnetic environmental noise by setting the distance between the magnetic field measurement points at substantially the same size of a lymph node.

Furthermore, it is an object of the present invention to provide a magnetic fluid detection method and magnetic fluid detection apparatus which can detect a magnetic fluid using an inexpensive magnetic field sensor with a low sensitivity by increasing the intensity of the applied magnetic field, so that sentinel lymph node biopsies can be popularized.

The magnetic fluid detection method of the present invention comprises: a step in which a magnetic fluid possessing magnetism is injected from the outside into a substance in which flow of the fluid is possible, an excitation step in which a direct-current or alternating-current magnetic field is used in order to excite the abovementioned magnetic fluid is applied; a measurement step in which the variation in the magnetic field strength caused by the applied magnetic field is measured in two or more places that are in close proximity; an amplification step in which the difference between the signals measured in the abovementioned measurement step is amplified; a calculation step in which the absolute value or amplitude value of the signal amplified in the abovementioned amplification step is calculated; and a search step in which a search is made for a portion of the substance where the abovementioned calculation step shows a maximum value by interlockingly moving the portion excited in the abovementioned excitation step and the portion measured in the abovementioned measurement step. In this method, the portion of the abovementioned substance in which the largest amount of the magnetic fluid has accumulated is identified by measuring the distortion of the local magnetic field distribution that results from the fact that the specific magnetic permeability of the abovementioned magnetic fluid is higher than that of the surrounding substance.

Furthermore, the magnetic fluid detection apparatus of the present invention comprises: an excitation device which applies a direct-current or alternating-current magnetic field for the purpose of performing magnetic fluid excitation on an object to be measured in which a magnetic fluid possessing magnetism is injected from the outside and in which a fluid can flow; measuring devices which measure the variation in the magnetic field strength caused by the magnetic field applied by the abovementioned excitation device in two or more places; a differential amplifier which receives signals from the measuring devices obtained in the abovementioned two or more places and amplifies the difference signal; a calculating unit which receives signals from the abovementioned differential amplifier and calculates the absolute value or amplitude value of the signal strength; and a display device which receives signals from the abovementioned calculating unit and displays a numerical value or waveform. In this apparatus, sites where the largest amount of the abovementioned magnetic fluid has accumulated inside the abovementioned substance are identified by measuring the distortion of the local magnetic field distribution caused by the fact that the specific magnetic permeability of the abovementioned magnetic fluid is higher than that of surrounding substance.

Furthermore, the magnetic fluid detection method of the present invention comprises: a step in which a magnetic fluid possessing magnetism is caused to accumulate in sentinel lymph nodes from the outside; an excitation step in which a direct-current or alternating-current magnetic field that is used to excite the abovementioned magnetic fluid is applied; a measurement step in which the variation in the magnetic field strength caused by the applied magnetic field is measured in two or more places that are in close proximity; an amplification step in which the difference between the signals measured in the abovementioned measurement step is amplified; a calculation step in which the absolute value or amplitude value of the signal amplified in the abovementioned amplification step is calculated; and a search step in which a search is made for a portion of the substance where the abovementioned calculation step shows a maximum value by interlockingly moving the portion excited in the abovementioned excitation step and the portion measured in the abovementioned measurement step. In this method, sentinel lymph nodes in which the magnetic fluid has accumulated are identified by measuring the distortion of the local magnetic field distribution that results from the fact that the specific magnetic permeability of the abovementioned magnetic fluid is higher than that of the surrounding substance.

Furthermore, the magnetic fluid detection apparatus of the present invention comprises: an excitation device which applies a direct-current or alternating-current magnetic field used for magnetic fluid excitation to living-body tissues in which a magnetic fluid possessing magnetism has been injected into areas proximal to a malignant tumor; measuring devices which measure the variation in the magnetic field strength caused by the magnetic field applied by the abovementioned excitation device in two or more places; a differential amplifier which receives signals from the measuring devices obtained in the abovementioned two or more places and amplifies the difference signal; a calculating unit which receives signals from the abovementioned differential amplifier and calculates the absolute value or amplitude value of the signal strength; and a display device which receives signals from the abovementioned calculating unit and displays a numerical value or waveform. In this apparatus, sentinel lymph nodes constituting sites where the largest amount of the abovementioned magnetic fluid has accumulated are identified by measuring the distortion of the local magnetic field distribution caused by the fact that the specific magnetic permeability of the abovementioned magnetic fluid is higher than that of the surrounding substance.

The above and other objects, features and advantages of the invention will become more clearly understood from the following description referring to the accompanying drawings.

DESCRIPTION OF THE PREFERRED EMBODIMENTS

An embodiment of the present invention will be described in detail below with reference to the attached figures. Furthermore, the same or corresponding parts in the figures are labeled with the same symbols, and a description of these parts is omitted.

Figure 3:
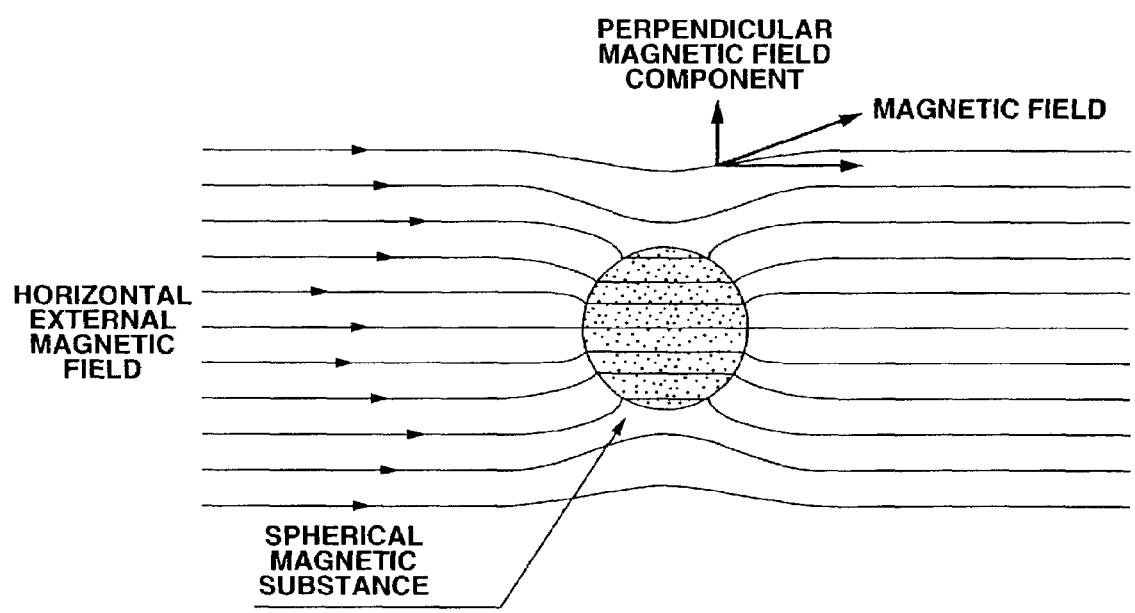
FIG. 3 is an explanatory diagram which illustrates the measurement principle of the present invention.

FIG. 3 is a diagram which illustrates the measurement principle of the present invention.

Referring to FIG. 3, almost all organic compounds that make up the living body, as well as non-magnetic metals such as copper and aluminum, have a specific magnetic permeability of approximately 1, and therefore cause almost no distortion of magnetic fields. On the other hand, in the case of a magnetic fluid possessing paramagnetism, the surrounding magnetic field is drawn in on itself as shown in FIG. 3 as a result of the presence of fine magnetic particles with a specific magnetic permeability that is greater than 1, so that there is a distorting effect on the magnetic field.

FIG. 3 shows how the applied magnetic field is distorted in cases where an accumulation of stagnant magnetic fluid is present inside a substance 1 when a horizontal external magnetic field is applied to the substance 1 as a whole.

The distortion of the magnetic field occurs only while the magnetic fluid is being excited by the application of a magnetic field from the outside. Slight residual magnetization characteristics are shown when the particle size of the fine magnetic particles is greater than 10 nm; however, the strength of the residual magnetization is weak compared to the strength of the exciting magnetic field, so that an ultra-high-sensitivity magnetic sensor such as a SQUID (superconducting quantum interference device) is required in order to detect the residual magnetic field.

On the other hand, if the magnitude of the specific magnetic permeability $\mu$ is approximately 3 to 5, the magnetism-distorting effect of the abovementioned paramagnetic material can be measured even by means of an inexpensive magnetic sensor with poor sensitivity such as a Hall element or magnetic resistance element.

Figure 1:
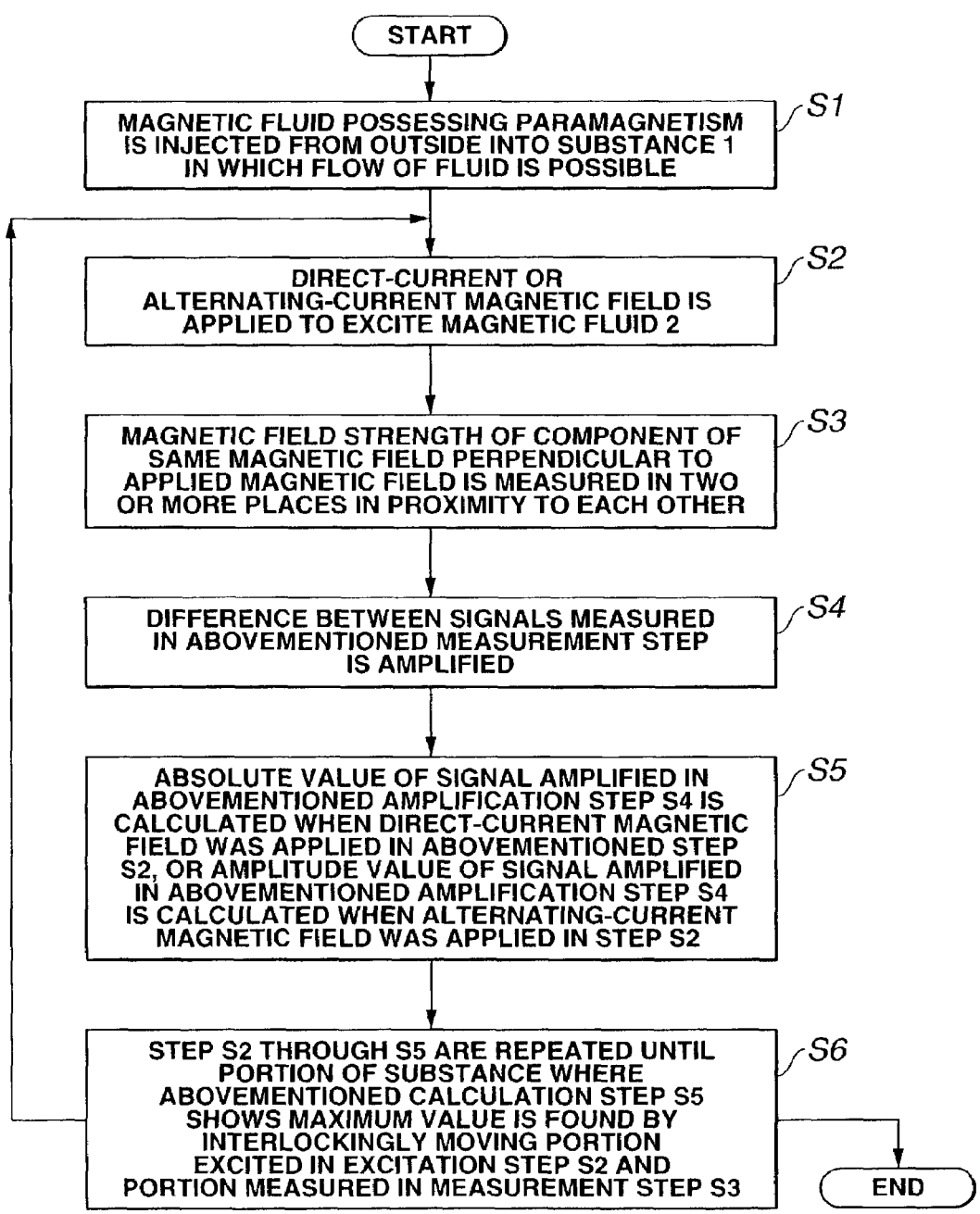
FIG. 1 is a flow chart which illustrates the operation of a magnetic fluid detection method according to one embodiment of the present invention.

FIG. 1 is a block diagram which illustrates the operation of the magnetic fluid detection method according to an embodiment of the present invention.

Referring to FIG. 1, first, in the injection step S1, a magnetic fluid 2 possessing paramagnetism is injected from the outside into the substance 1 (living-body tissue) in which a fluid can flow. Next, in the excitation step S2, a direct-current or alternating-current magnetic field which is used to excite the abovementioned magnetic fluid 2 is applied. Furthermore, in the measurement step S3, the magnetic field strength of the component in the same magnetic field direction that is perpendicular to the applied magnetic field is measured in two or more places that are in close proximity to each other. In the amplification step S4, the difference between the signals measured in the abovementioned measurement step is amplified. Then, in the calculation step S5, the absolute value of the signal amplified in the abovementioned amplification step S4 is calculated when a direct-current magnetic field was applied in the abovementioned excitation step S2, or the amplitude value of the signal amplified in the abovementioned amplification step S4 is calculated when an alternating-current magnetic field was applied in the abovementioned excitation step S2. In the search step S6, a repeated search is made for the portion of the substance where the abovementioned calculation step S5 shows a maximum value, this search being accomplished by interlockingly moving the portion excited in the abovementioned excitation step S2 and the portion measured in the abovementioned measurement step S3.

In the abovementioned embodiment, the portion showing the largest distortion of the local magnetic field distribution arising from the fact that the specific magnetic permeability of the abovementioned magnetic fluid 2 is higher than that of the surrounding substance can be identified. Specifically, the portion where the largest amount of magnetic fluid has accumulated inside the substance can be identified. In concrete terms, in the abovementioned search step S6, judgement by the operator can be facilitated by display processing involving conversion into numerical values or a graph. Alternatively, in a case where the absolute value of the signal or the exciting magnetic field is an alternating-current magnetic field, the portion of the substance where the abovementioned calculation step S5 shows a maximum value can be found using the auditory sense of the operator by outputting a sound with the frequency, intensity or sounding interval of this sound varied on the basis of the amplitude value of the signal.

To describe this in more detail, portions of the tissue in which a large amount of the magnetic fluid has accumulated can be identified by varying the positions of magnetic field application and magnetic field strength measurement in order to find the portion where the greatest variation in numerical values or the greatest variation in waveform occurs. The positions of sentinel lymph nodes can be identified by injecting a magnetic fluid into malignant tumor sites, and then applying the magnetic fluid detection method of the present invention to the surrounding lymph nodes after a fixed period of time has elapsed.

For example, in a case where the applied magnetic flux density is set at approximately 800 gauss to 1300 gauss (approximately 0.08 tesla to 0.13 tesla), and the magnetic field component perpendicular to the applied magnetic field is measured at positions separated by 5 mm using measurement means such as a Hall element or magnetic resistance element, sites where the magnetic fluid is present can be measured without any effect of magnetic environmental noise by amplifying the difference between the two magnetic sensor outputs by an amplification rate of 1,000 times to 10,000 times. In a case where lymph nodes are the object of examination, the greatest reduction in the effect of magnetic environmental noise can achieved by setting the distance between the two sensors at approximately 5 mm to 10 mm.

Figure 2:
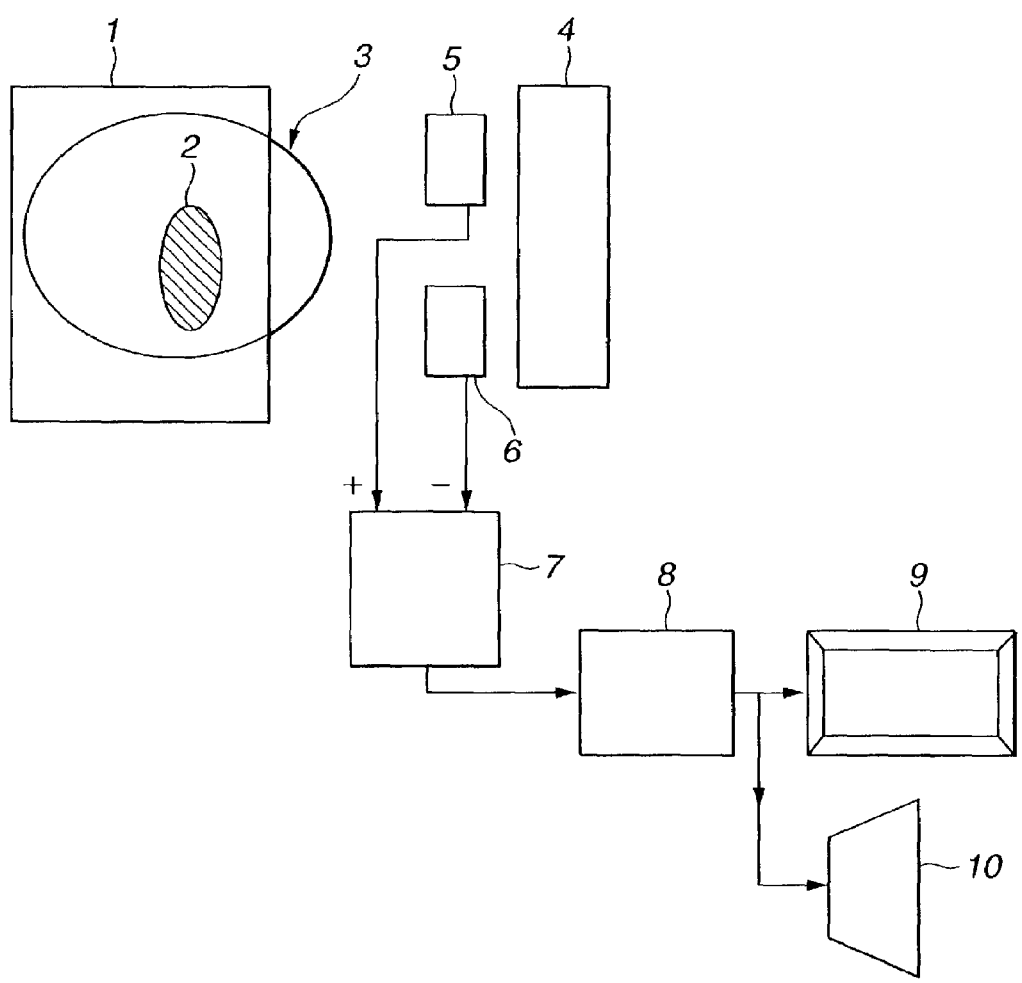
FIG. 2 is a block diagram which shows the construction of a magnetic fluid detection apparatus constructed according to one embodiment of the present invention.

FIG. 2 is a block diagram which shows the magnetic fluid detection apparatus constituting an embodiment of the present invention in more concrete terms.

Referring to FIG. 2, an excitation device 4 is a functional block which applies a direct-current or alternating-current exciting magnetic field to a region 3 constituting the object of measurement, in which the magnetic fluid 2 possessing paramagnetism has been injected from the outside into the substance 1 (living-body tissue) in which a fluid can flow. The object of this functional block is excitation of the abovementioned magnetic fluid 2. To describe this in more detail, when a direct-current magnetic field is applied, a neodymium magnet can be used in order to apply the magnetic field used for excitation. Furthermore, a magnetic flux density of around 1 tesla can be generated by forming a magnetic core with a diameter of about 10 mm using an amorphous or nano-size particulate magnetic material with a small core loss whose specific magnetic permeability $\mu$ is on the order of 10,000 to 100,000, and by applying a direct current or alternating current with a current strength or current amplitude of approximately 10 mA to a solenoid coil of approximately 80 turns.

A measuring device 5 and measuring device 6 are functional blocks which measure the component of the same magnetic field that is perpendicular to the applied magnetic field in two or more places that are located in close proximity to each other. When the magnetic fluid has a Feridex concentration of 1,000 to 10,000 ppm, these functional blocks can be constructed using Hall elements or magnetic resistance elements as magnetic sensors that have a magnetic flux resolution of several tens of microgauss.

A differential amplifier 7 is a functional block which receives the signals from the abovementioned measuring device 5 and the abovementioned measuring device 6, and which amplifies the difference signal. When the magnetic fluid has a Feridex concentration of 1,000 to 10,000 ppm, an output signal with a level of several volts can be obtained by setting the amplification rate of the differential amplifier at approximately 1,000 times to 10,000 times.

If the distance between the magnetic resistance elements is set at approximately 5 mm to 10 mm, commercial alternating-current noise which accounts for almost all magnetic environmental noise will not impede the measurement. The reason for this is as follows: namely, the noise sources are considerably more distant than the object of measurement, and since magnetic noise of approximately the same intensity is admixed in both the measuring device 5 and measuring device 6, these noise components substantially cancel each other when the difference between the two signals is taken. On the other hand, if an accumulation of the magnetic fluid 2 is sufficiently close to one of the measuring devices 5 or 6, a magnetic field component that is perpendicular to the applied magnetic field is generated as shown in FIG. 3 as a result of the distorting effect exerted on the applied magnetic field by the magnetic fluid 2, so that a spatial magnetism gradient is generated; accordingly, a difference signal can be obtained by the differential amplifier 7 with a sufficient S/N ratio.

A calculating unit 8 is a functional block which receives the signal from the abovementioned differential amplifier 7, and which calculates the absolute value of the signal strength when the exciting magnetic field is a direct-current magnetic field, or the amplitude value of the amplified difference signal when the exciting magnetic field is an alternating-current magnetic field. This functional block can easily be realized by means of a full-wave rectifying circuit or synchronized detection circuit using transistors or diodes.

A display device 9 is a functional block which receives signals from the abovementioned calculating unit 8, and converts these signals into a visual display in order to display numerical values or waveforms.

Furthermore, an acoustic conversion device (speaker) 10 is a functional block which receives signals from the abovementioned calculating unit 8, and which outputs sound with the frequency, intensity or sounding interval of this sound varied in proportion to the absolute value of the signal strength when the exciting magnetic field is a direct-current magnetic field, or in proportion to the amplitude value of the amplified difference signal when the exciting magnetic field is alternating-current magnetic field, in order to make it possible for the operator to find, using only his auditory sense, the portion of the substance 1 in which the greatest amount of the magnetic fluid 2 has accumulated. As a result, the operating characteristics of the operation used to identify sites where the greatest amount of the magnetic fluid 2 has accumulated inside the substance 1 can be greatly improved.

When measurements are performed using the magnetic fluid detection apparatus constructed as described above, a large variation is generated in the detection signal in areas where the magnetic fluid has accumulated at a high concentration. Accordingly, since the magnetic fluid accumulates most readily in sentinel lymph nodes, sentinel lymph nodes can be identified quickly, safely and with high precision by injecting a magnetic fluid into the vicinity of a malignant tumor, and then performing measurements after an appropriate period of time has elapsed.

Figure 4:
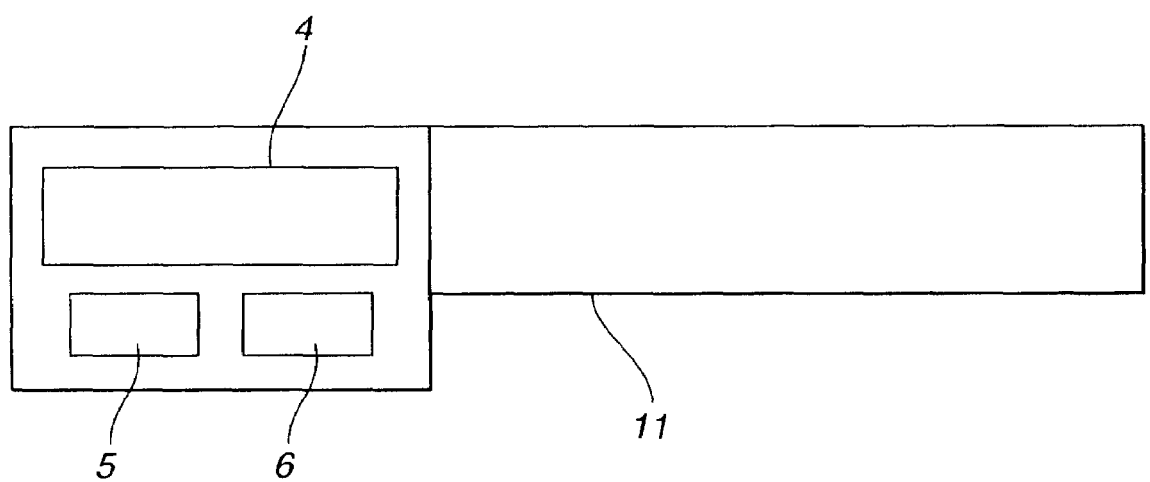
FIG. 4 is a diagram which shows the three-dimensional schematic construction of a case that accommodates the magnetic field excitation means 4, measurement means 5 and measurement means 6 of the magnetic fluid detection apparatus shown in FIG. 2.

Furthermore, as shown in FIG. 4, if at least the portion of the abovementioned excitation device 1 that generates a magnetic field, as well as the measuring device 5 and measuring device 6, are accommodated as an integral unit and installed in a case 11 with a toothbrush shape, pencil shape or pistol shape that can be held in one hand, the operator can easily hold this integrated device in one hand, so that the work of identifying sentinel lymph nodes that are the object of sentinel lymph node biopsies can be performed quickly and safely.

Especially when the shape of the magnetic field detection portion is a toothbrush shape, measurements can be performed in a comfortable standing position, so that the burden on the physician is alleviated.

Furthermore, the acoustic conversion device 10 shown in FIG. 2 is a functional block which is characterized in that this device receives signals from the differential amplifier 7, and outputs sound with the frequency, intensity or sounding interval of this sound varied in proportion to the absolute value of the signal strength, or in proportion to the amplitude value of the amplified difference signal when the exciting magnetic field is an alternating-current magnetic field. If such a functional block is provided, the differential magnetic field strength or amplitude is converted into sound, so that the operator can ascertain the measurement results simply by listening to variations in this sound. Consequently, the physician can concentrate his attention on the condition of the measurement sites; accordingly, not only is safety improved, but the burden on the physician is alleviated.

Thus, in the abovementioned embodiment of the present invention, the presence of a magnetic fluid can be measured using a Hall element or magnetic resistance element which is a magnetic sensor that is less sensitive and less expensive than a SQUID. Since there is no need for any cooling means, through there is in the case of a SQUID magnetic flux meter, handling is simple, and the apparatus can be constructed with a weight and shape that easily allow the apparatus to be held in one hand. The system as a whole is also inexpensive, and there is no need for a shielded room in order to reduce magnetic environmental noise.

Thus, the question of whether or not the lymph nodes that are examined are sentinel lymph nodes can be decided quickly and with high precision without using a radioactive isotope as a marker. Furthermore, there are no problems even when the lymph nodes are black and difficult to distinguish using dyes.

In the case of the magnetic fluid detection method and magnetic fluid detection apparatus of the abovementioned embodiment of the present invention, the operator can easily hold the apparatus in one hand; accordingly, sentinel lymph nodes that are the object of a sentinel lymph node biopsy can be identified quickly and safely during a surgical operation.

Especially in cases where the shape of the magnetic field detection portion is a toothbrush shape, measurements can be performed in a comfortable standing position, so that the burden on the physician is alleviated. Furthermore, as a result of the differential magnetic field strength or amplitude being converted into sound, the physician can concentrate his attention on the condition of the measurement sites; accordingly, not only is safety improved, but the burden on the physician is alleviated.

The embodiment disclosed above is an example in all respects, and should not be viewed as limiting the present invention. The scope of the present invention is indicated by the claims, and not by the abovementioned description. It is intended that all alterations within a sense and scope that are equivalent to the scope of the claims be included in the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A magnetic fluid detection method comprising:
    a step in which a magnetic fluid possessing magnetism is injected from the outside into a substance in which the fluid can flow;
    an excitation step in which a direct-current or alternating-current magnetic field for exciting said magnetic fluid is applied;
    a measurement step in which the variation in the magnetic field strength caused by the applied magnetic field is measured in two or more places that are close to each other, the measurement of the variation of the magnetic field strength is of a component of the magnetic field strength that is perpendicular to the applied magnetic field, a distance between the magnetic field strength measurement places is set approximately equal to the substantial size of the areas where the magnetic fluid accumulates;
    a calculation step in which the absolute value or amplitude value of signals measured in said measurement step is calculated; and
    a search step in which a search is made for a portion of the substance where said calculation step shows a maximum value by interlockingly varying a position of the magnetic field application in the excitation step and the magnetic field strength measurement in the measurement step;
    wherein said portion of said substance in which the largest amount of the magnetic fluid has accumulated are identified by measuring the distortion of the local magnetic field distribution that results from the fact that the specific magnetic permeability of said magnetic fluid is higher than that of the surrounding substance.

2. The magnetic fluid detection method according to claim 1, wherein the calculation step amplifies the difference between the signals measured in said measurement step.

3. The magnetic fluid detection method according to claim 2, wherein the portion of the substance in which said calculation step shows a maximum value is found by outputting sound, with the frequency, intensity or sounding interval of this sound varied on the basis of the absolute value of the signal, or on the basis of the amplitude value of the amplified difference signal when the exciting magnetic field is an alternating-current magnetic field.

4. The magnetic fluid detection method according to claim 2, wherein said search step is accomplished by a display-processing based on conversion into numerical values or a graph.

5. The magnetic fluid detection method according to claim 2, wherein the portion of the substance in which a great amount of the magnetic fluid has accumulated is identified by varying the position of magnetic field application and magnetic field strength measurement in order to find the portion showing the greatest variation in numerical values or variation in waveform.

6. The magnetic fluid detection method according to claim 1, wherein said search step is accomplished by a display-processing based on conversion into numerical values or a graph.

7. The magnetic fluid detection method according to claim 1, wherein the portion of the substance in which a great amount of the magnetic fluid has accumulated is identified by varying the position of magnetic field application and magnetic field strength measurement in order to find the portion showing the greatest variation in numerical values or variation in waveform.

8. A magnetic fluid detection apparatus comprising:
    an excitation device which applies a direct-current or alternating-current magnetic field for the purpose of magnetic fluid excitation to an object of measurement in which a magnetic fluid possessing magnetism is injected from the outside into a substance in which a fluid can flow;
    measuring devices which measure the variation in the magnetic field strength caused by the magnetic field applied by said excitation device in two or more places, the measurement of the variation of the magnetic field strength is of a component of the magnetic field strength that is perpendicular to the magnetic field applied, a distance between said measuring devices is set substantially equal to the size of the site in which the magnetic fluid accumulates, the measurement of the variation of the magnetic field strength at each of the two or more places being performed interlockingly with a variation in position of the magnetic field application by the excitation device;
    a differential amplifier which receives signals from the measuring devices in said two or more places and amplifies the difference signal;
    a calculating unit which receives signals from said differential amplifier and calculates the absolute value or amplitude value of the signal strength; and
    a display device which receives signals from said calculating unit and displays a numerical value or waveform;
    wherein site where the largest amount of said magnetic fluid has accumulated inside said substance is identified by measuring the distortion of the local magnetic field distribution caused by the fact that the specific magnetic permeability of said magnetic fluid is higher than that of the surrounding substance.

9. The magnetic fluid detection apparatus according to claim 8, wherein at least the portion of said excitation device that generates a magnetic field, and the measuring devices that perform measurements in two or more places, are accommodated into an integral unit in a toothbrush shape, pencil shape or pistol shape which allows the apparatus to be gripped with one hand, in order to improve the operating characteristics of the operation used to identify the site where the largest amount of said magnetic fluid has accumulated inside said substance.

10. The magnetic fluid detection apparatus according to claim 9, wherein the apparatus is equipped with an acoustic conversion device which receives signals from said calculating unit, and outputs a sound with the frequency, intensity or sounding interval of this sound varied in proportion to the absolute value or amplitude value of the signal strength.

11. The magnetic fluid detection apparatus according to claim 8, wherein the excitation device and the measuring device are integrally formed.

12. A magnetic fluid detection method comprising:
- a step in which a magnetic fluid possessing magnetism is caused to accumulate in sentinel lymph nodes from the outside;
- an excitation step in which a direct-current or alternating-current magnetic field for exciting said magnetic fluid is applied;
- a measurement step in which the variation in the magnetic field strength caused by the applied magnetic field is measured in two or more places that are proximal to each other, the measurement of the variation of the magnetic field strength is of a component of the magnetic field strength that is perpendicular to the applied magnetic field, a distance between said magnetic field strength measurement places is set substantially equal to the size of the site in which the magnetic fluid accumulates;
- an amplification step in which the difference between the signals measured in said measurement step is amplified;
- a calculation step in which the absolute value or amplitude value of the signal amplified in said amplification step is calculated; and
- a search step in which a search is made for portion where said calculation step shows a maximum value by interlockingly varying a position of the magnetic field application in the excitation step and the magnetic field strength measurement in the measurement step;
- wherein sentinel lymph nodes in which the magnetic fluid has accumulated are identified by measuring the distortion of the local magnetic field distribution that results from the fact that the specific magnetic permeability of said magnetic fluid is higher than that of the surrounding substance.

13. A magnetic fluid detection apparatus comprising:
- an excitation device which applies a direct-current or alternating-current magnetic field for magnetic fluid excitation to living-body tissues in which a magnetic fluid possessing magnetism has been injected into areas proximal to a malignant tumor;
- measuring devices which measure the variation in the magnetic field strength caused by the magnetic field applied by said excitation device in two or more places, the measurement of the variation of the magnetic field strength is of a component of the magnetic field strength that is perpendicular to the magnetic field applied, the measurement of the variation of the magnetic field strength at each of the two or more places being performed interlockingly with a variation in position of the magnetic field application by the excitation device, a distance between said measuring devices is set approximately equal to the size of the sites in which the magnetic fluid accumulates;
- a differential amplifier which receives signals from the measuring devices in said two or more places and amplifies the difference signal;
- a calculating unit which receives signals from said differential amplifier and calculates the absolute value or amplitude value of the signal strength;
- and a display device which receives signals from said calculating unit and displays a numerical value or waveform;
- wherein sentinel lymph node which is the site where the largest amount of said magnetic fluid has accumulated is identified by measuring the distortion of the local magnetic field distribution caused by the fact that the specific magnetic permeability of said magnetic fluid is higher than that of the surrounding substance.

14. The magnetic fluid detection apparatus according to claim 13, wherein at least the portion of said excitation device that generates a magnetic field, and the measuring devices that perform measurements in two or more places, are accommodated into an integral unit in a toothbrush shape, pencil shape or pistol shape which allows the apparatus to be gripped with one hand, in order to improve the operating characteristics of the operation used to identify the sites where the largest amount of said magnetic fluid has accumulated inside said substance.

15. The magnetic fluid detection apparatus according to claim 13, wherein the apparatus is equipped with an acoustic conversion device which receives signals from said calculating unit, and outputs a sound with the frequency, intensity or sounding interval of this sound varied in proportion to the absolute value or amplitude value of the signal strength.

16. The magnetic fluid detection apparatus according to claim 13, wherein the excitation device and the measuring device are integrally formed.

* * * * *